(12) United States Patent
Widmer et al.

(10) Patent No.: US 7,185,734 B2
(45) Date of Patent: Mar. 6, 2007

(54) HEARING PROTECTION EARPLUG, USE OF SUCH AN EARPLUG AND METHOD FOR MANUFACTURING SUCH AN EARPLUG

(75) Inventors: Christoph Widmer, Wernetshausen (CH); Christian Berg, Uerikon (CH)

(73) Assignee: Phonak AG, Staefa (CH)

( * ) Notice: Subject to any disclaimer, the term of this patent is extended or adjusted under 35 U.S.C. 154(b) by 211 days.

(21) Appl. No.: 10/925,137

(22) Filed: Aug. 25, 2004

(65) Prior Publication Data

US 2006/0042866 A1   Mar. 2, 2006

(51) Int. Cl.
*A61B 7/02* (2006.01)
(52) U.S. Cl. .................. 181/135; 128/864; 381/328
(58) Field of Classification Search ............. 181/135; 128/864; 381/328
See application file for complete search history.

(56) References Cited

U.S. PATENT DOCUMENTS

| | | | | |
|---|---|---|---|---|
| 4,353,364 A | * | 10/1982 | Woods | 128/867 |
| 4,807,612 A | * | 2/1989 | Carlson | 128/868 |
| 5,074,375 A | * | 12/1991 | Grozil | 181/135 |
| 5,763,503 A | | 6/1998 | Cowperthwaite et al. | |
| 6,082,485 A | * | 7/2000 | Smith | 181/135 |
| 6,339,648 B1 | * | 1/2002 | McIntosh et al. | 381/328 |
| 6,533,062 B1 | | 3/2003 | Widmer et al. | |
| 6,687,377 B2 | | 2/2004 | Voix et al. | |
| 2002/0179365 A1 | * | 12/2002 | Meussen et al. | 181/135 |
| 2003/0051939 A1 | * | 3/2003 | Werblud | 181/131 |
| 2003/0112990 A1 | | 6/2003 | McIntosh et al. | |
| 2003/0133583 A1 | | 7/2003 | Widmer et al. | |
| 2004/0257233 A1 | * | 12/2004 | Proebsting | 340/573.1 |

FOREIGN PATENT DOCUMENTS

| | | |
|---|---|---|
| DE | G 93 13 061.9 U1 | 1/1994 |
| FR | 2 849 771 A1 | 7/2004 |
| GB | 2 373 951 A | 10/2002 |

* cited by examiner

*Primary Examiner*—Lincoln Donovan
*Assistant Examiner*—Forreest Philips
(74) *Attorney, Agent, or Firm*—David S. Safran

(57) ABSTRACT

The invention relates to a hearing protection earplug, comprising a shell for being worn at least in part in the ear canal of a user and a faceplate (12) at the outer end of the shell or within a cavity of the shell having an outer opening, wherein the faceplate is provided with adapter means (22) for acoustically connecting, in a detachable manner, a measuring hole (14) extending into the interior of the shell with an external measuring tube (26). The adapter means (22) are adapted to detachably connect to a removable multi-function plug (28, 40) comprising means (30) for closing the measurement hole (14). The invention also relates to a use of such an earplug, a method for manufacturing such an earplug and to a multi-function plug to be used with such an earplug.

21 Claims, 3 Drawing Sheets

FIG. 1
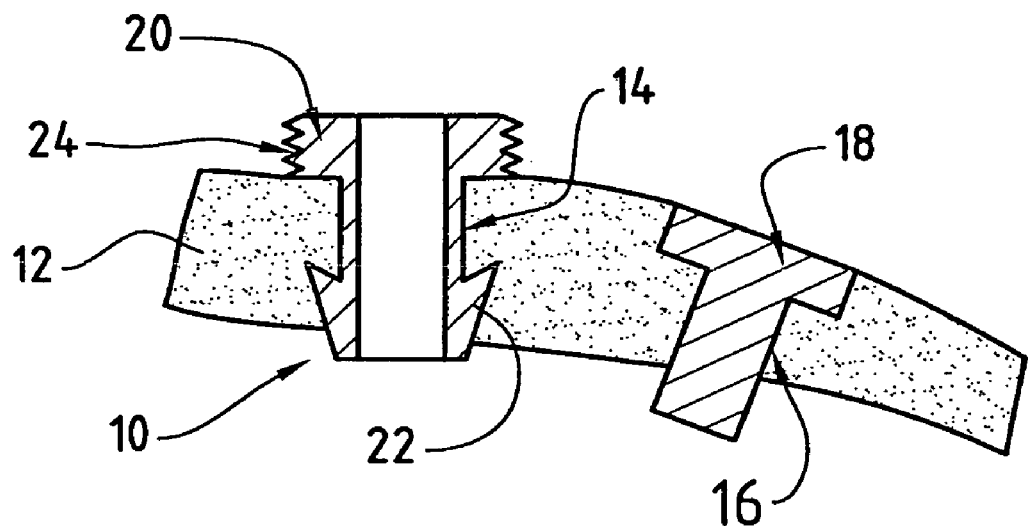
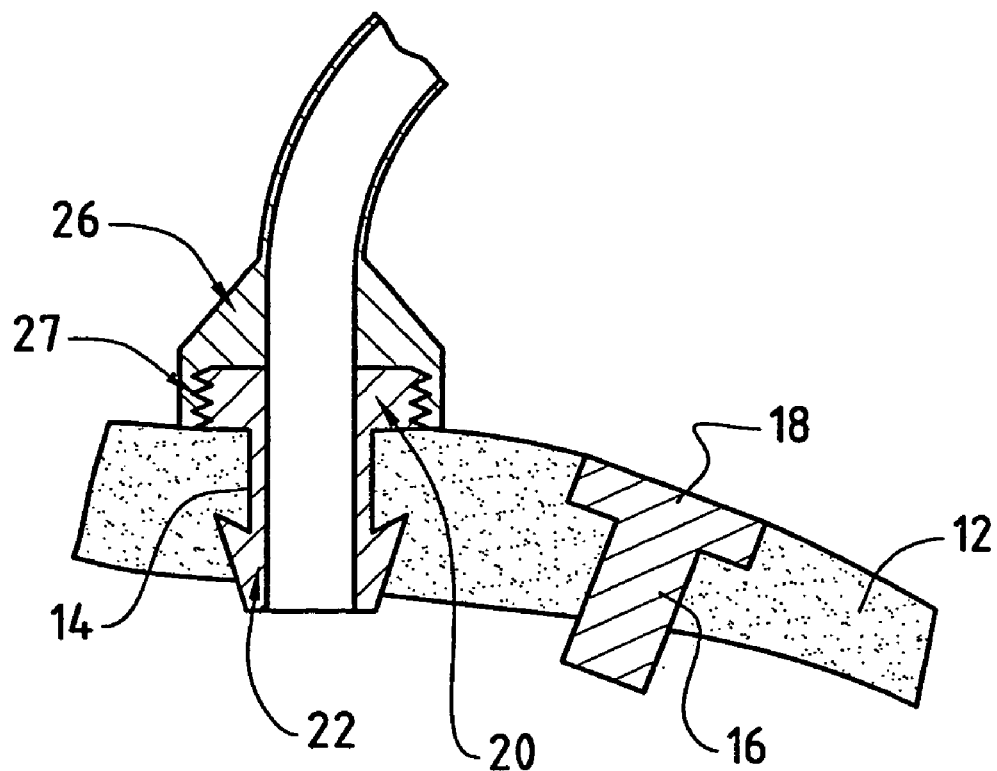
FIG. 2

FIG. 3
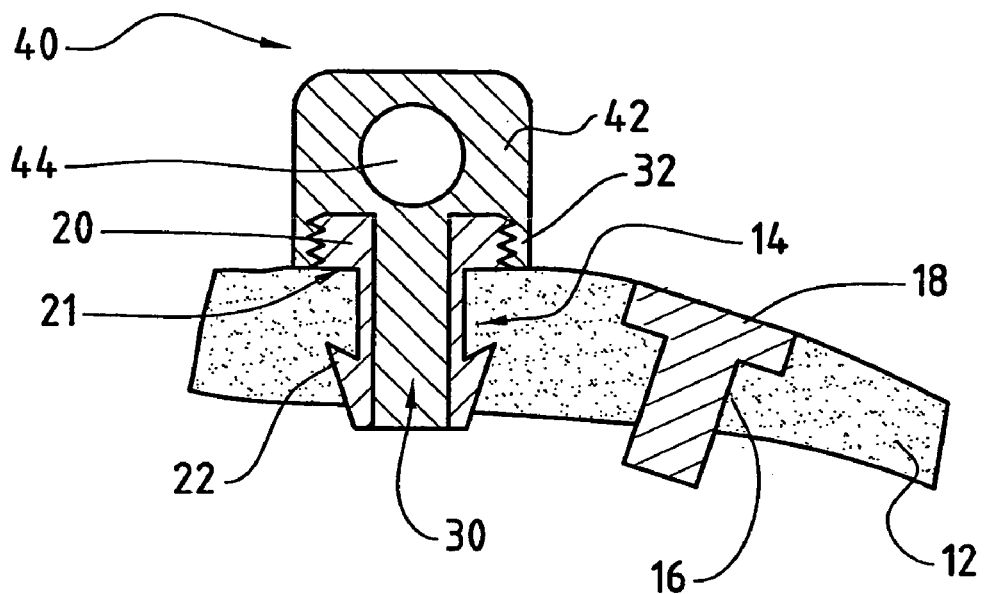
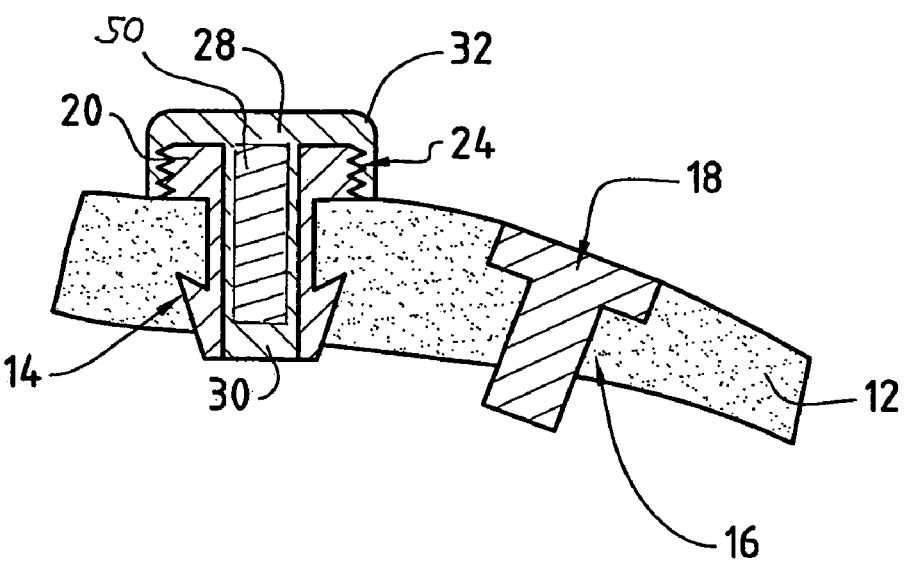
FIG. 4

HEARING PROTECTION EARPLUG, USE OF SUCH AN EARPLUG AND METHOD FOR MANUFACTURING SUCH AN EARPLUG

BACKGROUND OF THE INVENTION

1. Field of the Invention

The present invention relates generally to hearing protection earplugs comprising a shell for being worn at least in part in the ear canal of a user and a faceplate at the outer end of the shell or within a cavity of the shell having an outer opening, and is specifically directed to such hearing protection earplugs which allow for in-situ measurements within the shell and/or the ear canal. The invention is further relates a corresponding manufacturing method and to a use of such earplugs.

2. Description of Related Art

A large part of the population is exposed to hazardous noise from time to time. This can be at work, whilst traveling, during leisure activities or at home. The exposure can lead to permanent hearing loss, distract people's attention from other hazards or simply cause stress. In order to prevent both accidents and permanent hearing damage, hearing protection devices (HPDs) have been provided in many styles and over many years. It started with the earmuff which is still very relevant and addresses very noisy environments (e.g. airports, construction, shooting) or complex working/communication situations (e.g. fighter pilots). Over the years development of biocompatible soft materials has enabled soft earplugs in different styles and colors as well as recent development of "one fits many" standard semi-soft earplugs in silicon-rubber type materials. For severe situations even the combination of an earmuff and an "in-the-ear" HPD is required to achieve desired attenuation. The physical limitation of hearing protection based on ear worn devices is defined where bone-conduction (body acoustics) becomes dominant at around 40 dB attenuation.

A common disadvantage of the above mentioned HPD styles is wearing discomfort. In case of the earmuffs, they are large which creates difficulties in combination with other head worn gear and they "close off" the ear too much for most applications. The in-the-ear styles mentioned are devices made to fit "the average" ear in one way or the other. Either the fit is provided by softness of the material which leads to undefined device insertion and undefined attenuation, or the fit is provided by standard shaped structures intended to block off the ear canal. In both cases the flat distribution of the individual shape of the outer ear and the ear canal leads to bad fit, pressure points in the ear and undefined positioning of the device.

To address this wearing comfort issue, in-the-ear hearing aid technology has been applied making customized ear molds with passive acoustical filter. These are long lasting devices with good wearing comfort. However, this customization process is traditionally a very manual process creating varying results over time, low reproducibility and the quality is very operator skill dependent.

The basic idea to use rapid prototyping technology, such as layer-by-layer laser sintering of a powder material, in manufacturing customized shells, primarily for hearing aids, is described, for example, in U.S. Pat. No. 6,533,062 B1 or US 2003/0133583 A1. This technique is successfully being used in hearing aids and can be applied in a similar fashion for HPDs. By doing this, a whole new range of features and functions become feasible for HPDs.

Passive hearing protection devices (HPDs) exist in several forms. They range from a simple earplug made of synthetic foam to fully customized ear moulds with adjustable valves or adjustable attenuation, and from miniaturized invisible ear canal devices to large ear muffs.

Environmental sounds are typically comprised of a mixture of various sound wave frequencies having varying intensities. It is well documented that repeated or prolonged exposure to sounds of sufficiently high sound pressure level can cause temporary or permanent hearing impairment, i.e. can damage the auditory organ and cause serious hearing problems, including deafness. Harmful noise such as caused by explosions or bursts are often comprised of a mixture of sound wave frequencies of varying intensity. These disturbing frequencies are in both the high and low frequency bands and have sufficient intensity to cause hearing problems. Individuals who are frequently exposed to such disturbing and sometimes dangerous noise run the risk of incurring such injuries as hearing loss or even deafness. Such individuals include workers at demolition or construction sites, operators of heavy, noisy equipment and those in active military service. Ear (i.e. hearing) protection is needed to prevent a loss in hearing acuity and the gradual increase in the threshold of hearing resulting from extended exposures to loud noise.

Customized hearing protection devices, i.e. devices individually adapted to the user's ear, are higher priced devices compared to competing soft earplugs. Some of the higher value of such customized devices is defined in better anatomical fit of the device in the ear resulting in enhanced wearing comfort, but also a significant value add is linked to the better control of attenuation.

Usually, the desired sound or noise attenuation is defined by selection of an appropriate sound attenuation filter and, after the assembly of the device, the actually achieved attenuation is measured in-situ for confirmation. Hence customized HPDs mostly have a tube with the filter inserted in it for defined attenuation, and adjacent to this filter tube, a tube for the in-situ measurement of the actually obtained attenuation. This measurement tube should be closed for normal operation of the HPD.

It is usual to provide a pair of HPDs tethered together by means of a cord. Such a tethered earplug device will serve to prevent accidental dropping or loss thereof, be it the two or only one earplug of the pair. This is of importance, for instance, where the HPDs are to be used in an industrial food processing environment or in an environment where a dropped earplug would be likely to become so dirty that it is rendered unusable or lost altogether. In order to allow the fastening of such a security cord, the HPD must be equipped with a cord fastening means.

US 2003/0112990 A1 relates to a hearing protection earplug according to the preamble of claim 1, consisting of a core element surrounded by sleeve which is filled with a curable rubber-like material having a hardness value of less than shore A 30 for individually adapting the earplug to the shape of the user's ear canal and outer ear. The core element comprises a first sound bore which extends through the earplug and which may be detachably connected at its proximal end with a remote measurement apparatus and a second sound bore which is parallel to the first sound bore and which may be closed by an attenuation element or may serve for sound input by a hearing aid unit. The proximal end of the first sound bore is closed by a slit membrane when the first sound bore is not connected with the remote measurement apparatus.

It is an object of the present invention to provide for a hearing protection earplug enabling in-situ acoustic measurements and providing for at least one additional function, while having a compact design. It is a further object to provide for a corresponding manufacturing method and a use of such an earplug.

SUMMARY OF THE INVENTION

These objects are achieved by a hearing protection earplug as defined in claim 1, a use as defined in claim 17 and a manufacturing method as defined in claim 18. The invention is beneficial in that, by providing the faceplate with adapter means for acoustically connecting, in a detachable manner, a measuring hole with an external measuring tube, with the adapter means being adapted to detachably connect to a removable multi-function plug comprising means for closing said measurement hole, other functions, in addition to the in-situ measurement function provided by the adapter means, may be implemented in the removable multi-function plug, such as a cord attachment function or communication function. Since the adapter means are capable of alternatively fixing either the external measurement tube and the multi-function plug, no additional space is needed for the functions provided by the multi-function plug, whereby a compact design of the earplug, in particular compact design of the faceplate, where space is limited especially for in-the-ear earplugs, is enabled.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 1 shows a longitudinal sectional view of a faceplate of a hearing protection earplug according to the invention with an in-situ measurement hole in an open condition;

FIG. 2 shows a view of the faceplate of FIG. 1 during an in-situ measurement;

FIG. 3 shows a view of the faceplate of FIG. 1 with a cord attachment and closure plug fastened;

FIG. 4 shows a view of the faceplate of FIG. 1, with the measurement hole being closed by a protecting plug;

FIGS. 1 to 4 illustrate an architecture which may be used for carrying out the invention. In the figures, identical or similar parts bear the same reference numerals. In the exemplary embodiment of FIG. 1, which is a longitudinal sectional view of the outer portion of a hearing protection earplug 10, more precisely of the faceplate 12 of the earplug 10, the plate 12 has two holes 14, 16. The holes 14, 16 can typically be circular. However, by using for example laser sintering techniques it is easy to provide also other shapes for the holes 14, 16. The hole 16 is connected to a duct or in-situ measuring channel (not shown in FIGS. 1 to 4) leading into the ear canal whereas hole 14 is provided for being temporarily connected with a flexible tube for acoustic attenuation measurements.

Figure 5:
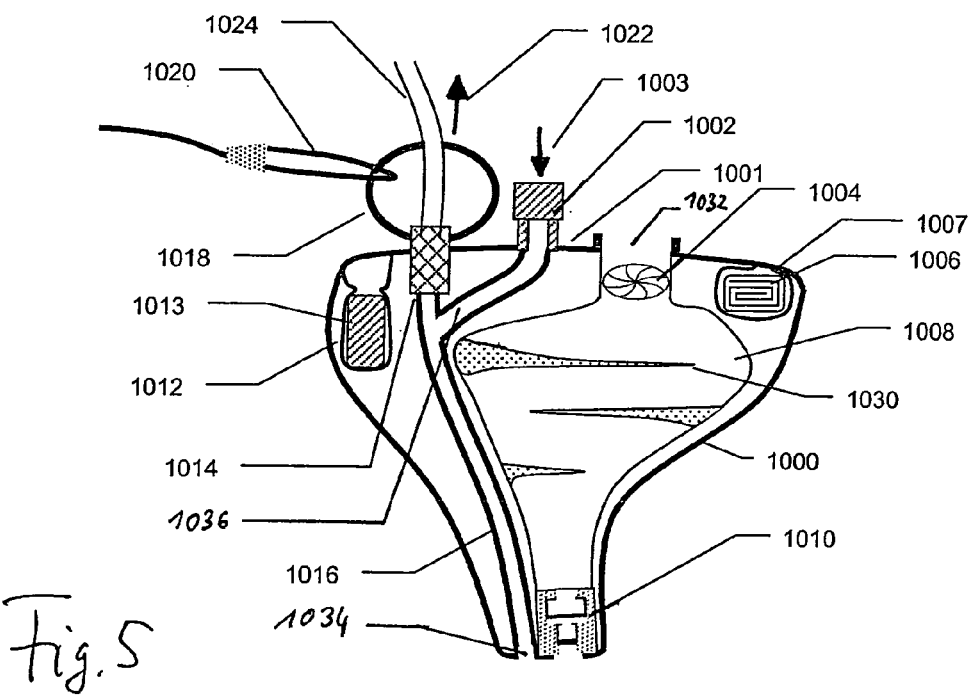
FIG. 5 shows a longitudinal sectional view of an example of a passive hearing protection earplug according to the invention when connected to an external measurement tube.

In a manner known per se, the hole 16 is closed by an acoustic attenuation filter device 18.

An adapter element 22 in the form of a hollow, generally cylindrical sleeve, is inserted into and fixed in hole 14 in a permanent or detachable manner, e.g. by cementing and/or gluing and/or snapping and/or bayonet coupling. However, it can also be provided as an integral part of the faceplate 12. The adapter element 22 has an outer annular circular flange 20 whose outer diameter is greater than that of the body of adapter element 22. The outer periphery of the flange 20 can be provided e.g. with a male thread 24. However also many other attachment concepts, e.g. garden water hose type adapters, etc. may be applied.

As it can be seen in FIG. 2, a connector 26 of a sound measuring tube has an inner female thread in its hollow cylindrical front portion. This thread is screwed upon the male thread 24 of the fitting flange 20 so that the measuring tube is firmly but in a removable manner connected to the faceplate and thus to the interior of the earplug 10.

When the measurement is finished, the tube connector 26 is screwed off, and the device is secured in that a screwable security plug 28 is screwed on the thread 24 of the fitting 22, see FIG. 4. The security plug 28 comprises a cylindrical stem 30 filling out the interior of the fitting element 22. The plug 30 further comprises an outer rim 32 bearing a female thread 27 on its inner peripheral surface so that the plug 28 can closely screwed in the manner of a cap onto the fitting element 22.

When the earplug 10 is to be used and to be connected to a cord, the plug 28 is unscrewed and replaced by an adapter plug 40 of this invention which is screwed on the thread 24 of the fitting element 22, see FIG. 3. This plug 40 is similar to plug 28 but is prolonged outwardly by a flat cord fastening tab 42. A cord fastening eyelet 44 is cut out of the flat tab 42. A security cord (not shown) that prevents the earplug from being lost can now be fastened in this eye in any desired manner. According to the invention, there are also many other alternatives conceivable, e.g. the tab is formed as a thread eye etc. In the same way, the tab 42 does not necessarily need to be flat but can have any other desired form.

The flat cord fastening tab may be replaced by a cylindrical stem protruding from the plug and having a transverse bore for attaching the security cord. This embodiment is not shown since it can be understood without drawing.

Further, the flat tab 42 that also serves as a handle for an easy application and removal of the combined plug 40 may be replaced by any other fastening element, e.g. a simple half-circular loop. Furthermore, the connecting threads 24, 27 may be replaced by any other connecting means known per se.

By using the plug 40 as a cord fixing means, strong fastening of the holding cord is achieved via the fixedly mounted adapter element 22. A further advantage is that the cord can easily be taken off either for replacement and/or service.

The security plug 28 may include a wireless communication device 50 as an additional function to the hole closing function, e.g. an active radio frequency device and antenna for e.g. one of the following standards or applications: Bluetooth, WLAN (Wireless Local Area Network), PLMN (Public Land Mobile Network) such as GSM (Global System for Mobile communication) or UMTS network (Universal Mobile Telephone System) or satellite based mobile network. It can also e.g. comprise passive radio frequency devices such as e.g. RFID (Radio Frequency Identification) devices. An RFID system typically consists of an antenna and a transceiver, which receive the radio frequency signal and transfer it e.g. to a processing device, and a transponder, or tag, which is an integrated circuit containing the RF circuitry and information to be transmitted. The tag can e.g. carry information such as an owner's or user's name and address and/or instructions or other information etc. The RFID tag integrated in the HPD can also be used to give e.g. other systems such as computer systems instructions on how to react automatically to certain conditions. The radio frequency devices can be unidirectional or bidirectional. The wireless communication device can of course also comprise e.g. a binaural data link and/or inductive receiver antenna such as the above mentioned RFID.

The external counterpart of the wireless communication device 50 of the security plug 28 is schematically shown at 52 in FIG. 4.

In general, the plate 12 may form the outer (i.e. proximal) end of the shell of the earplug or it may be recessed into the shell, i.e. it may be located at the bottom of a cavity of the shell having an outer opening for access to the plate 12.

In contrast to FIGS. 1 to 4, the filter device 18 need not be provided at the faceplate 12, but rather it may be located at a recessed position with a cavity of the shell.

As an alternative to providing for a cord fixation at the plug 40, a cord fixation, e.g. an eyelet, may be provided directly at the adapter element 22.

Preferably, the shell is a customized hard shell having an elasticity and a hardness from shore D 85 to shore D 65, for example, made of polyamide, and an outer surface individually shaped according to the measured inner shape of the user's outer ear and ear canal. The customized shell may be produced by an additive or incremental build-up process, such as layer-by-layer laser sintering (also known as "selective laser sintering") of a powder material. Such processes are described, for example in U.S. Pat. No. 6,533,062 B1.

FIG. 5 shows an example of a customized passive hearing protection earplug with a shell 1000 having a faceplate 1001 as its outer end and having a measuring channel 1016 formed integral with the shell 1000 and extending from a measuring hole with an adapter element 1014 to an opening at the inner (i.e. distal) end of the shell 1000. In FIG. 5, an external measuring tube 1024 is connected to the adapter element 1014 for connecting to the measuring channel 1016. The adapter element 1014 is provided with a cord fixation ring 1018 for fixing a neck cord 1020 at the shell 1000.

An acoustic attenuation filter 1010 is provided at the inner end of a resonance cavity 1008.

Figure 6:
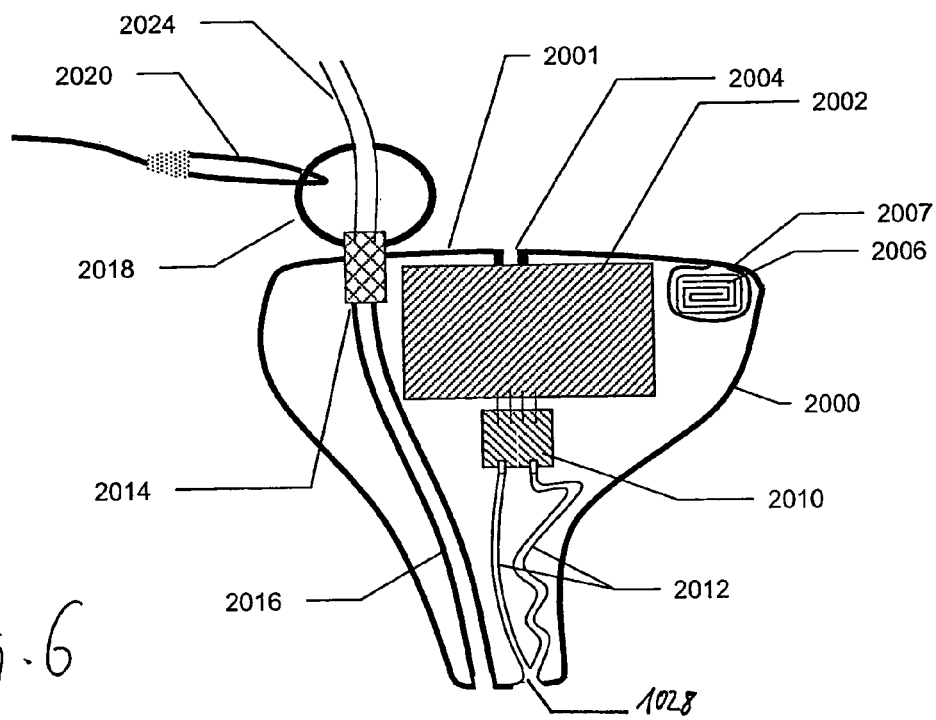
FIG. 6 shows a longitudinal sectional view of an example of an active hearing protection earplug according to the invention when connected to an external measurement tube.

In FIG. 6 an example of an active hearing protection earplug is shown wherein the customized shell 2000 is provided with a unit 2002 comprising active elements, such as a microphone, a battery, a digital signal processor for audio signal processing, control elements such as a volume control and a push button, and a programming interface, and with an electroacoustic output transducer unit 2010 with at least one speaker for sound output. These active components serve to selectively (i.e. temporarily and/or in a certain frequency range) by-pass the sound attenuation provided by the shell 2000. Similar to the embodiment of FIG. 5, the shell 2000 comprises a faceplate 2001 with an adapter element 2014 and an in-situ measuring channel 2016 which may be connected to an external measuring tube 2024. The adapter element 2014 may be connected to a fixation ring 2018 for a neck cord 2020.

In some applications, the measurement channel may terminate already within the interior of the shell for enabling measurements at cavities within the shell.

In addition to the features already mentioned, the embodiments of FIGS. 5 and 6 include some features which may be advantageously implemented by manufacturing the shell of the earplug by an additive build-up process, such as layer-by-layer laser sintering, by utilizing the option to shape and size the shell for functionality in addition to the individual optimized fit.

According to FIG. 5 the faceplate 1001 includes an outer sound input opening 1032 provided with a mechanical peak clipper 1004 and a sound inlet opening which is provided with a button 1002 which is manually operable in the direction 1003 to act as an attenuation button closing the sound inlet opening or as communication button opening the sound inlet opening for sound input into a sound passage 1036 which merges at its distal end with the in-situ measuring channel or tube 1016 which is acoustically connected to the measuring hole in adapter element 1014 and which extends to an inner sound opening 1034 at the inner end of the shell 1000. The sound input opening 1032 communicates with a resonance cavity 1008 with an inner mechanical structure 1030 for frequency tuning. At the distal end of the resonance cavity 1008 a semi-integrated passive acoustic filter 1010 is provided. The tubes 1036 and 1016 are formed integral with the shell 1000. Further, also an insert cavity 1007 for a RFID (radio frequency identification device)-tag 1006 and an insert cavity 1012 for a detectable metal part 1013 are formed integral with the shell 1000. While the neck cord 1020 is provided for preventing loss of the earplug, the ring 1018 or the cord 1020 also may serve to manually pull the earplug in the axial direction 1022.

According to FIG. 6, the output transducer unit 2010, may comprise several speakers/receivers which are acoustically connected via separate sound output channels 2012 to a sound output opening 2028. The faceplate 2001 includes a faceplate opening 2004 which may serve for sound input to the microphone of the active unit 2002 and/or for access to the programming interface, the volume control, the push button and/or the battery of the active unit 2002. Similar to the passive HPD of FIG. 6, a cavity 2007 for a RFID-tag 2006 is provided.

In the following these features and their functions will be explained in more detail.

Semi-Integrated Passive Filter

In passive HPDs acoustical filters mainly serve two purposes: firstly to define a certain amount of attenuation, secondly the filter can shape the frequency response of the attenuation in order to suppress some frequencies while letting others through (e.g. block low frequency noise and let speech pass above 1 kHz). The proposed base technology enables both usages of predefined component placement geometries (e.g. cavities 1012 for metal component 1013 insertion) as well as semi-integration of functions where the material itself becomes part of the solution (e.g. insert cavities, acoustical filters). The semi-integrated passive filter 1010 is a structure of the second kind, where the tubes are made in shell material while the membranes are inserted components. Selection of membranes can be done to order and individual need, hence the component remains customizable. The filter must be considered and dimensioned together with other filter means like the customizable front chamber shaping structure (or resonance cavity) 1008, 1030 (Helmholtz resonator) and the mechanical peak clipper 1004.

Communication/Attenuation Button

A core function of a passive HPD is to enable temporary audio bypass for purposes like listening to speech, alarm or other desired audio signals even though they are mixed with loud noise. This is often performed by a push/return-button opening a tube either bypassing the filter of the system or leading into the in-situ measurement probe tube 1016 on the inside of the closing plug to be connected to the adapter element 1014 when the measuring tube 1024 is removed. The integration of such a device into the faceplate 1001 overcomes many drawbacks of similar standard component solutions (e.g. complex tubing, acoustical leakage). An even more integrated solution is achieved by building the switch directly into the multipurpose cord adapter core element 1014 replacing the sealing plug. If the button is made of metal it could serve as a metal piece for the detection function, thereby eliminating the need for the metal part 1013.

Inverse Anatomy Force Button

A further level of integration of the on/off switch is based on the shell technology combined with the natural anatomy of the outer ear. In addition to a defined audio "leak" via a tube 1016 through the HPD, there is the alternative of creating a temporary leak between the device and the outer ear by slightly pulling the device out of the ear. This pull can be done by the cord 1020 or directly by grip and pull on the cord ring 1018. If the shell 1000 is shaped in an appropriate manner, the ear shape is such that the device will be naturally pulled back in place when the pull is relaxed.

Intelligent Passive HPD

Inserting a device into the ear principally blocks the acoustical tube (ear canal) and destroys the natural outer ear amplification and frequency shaping (open ear gain, OEG). The open ear has a natural resonance in the frequency area of the most critical speech information, hence this loss is a real loss and not normally desired. The resonance frequency is given by the length of the tube; hence there is a need for compensation of the reduced length. This can be individually modeled and implemented with a defined acoustical front (outer) chamber 1008 and artificially stretched to a desired length by a mechanical means 1030 for resonance shaping directly integrated into the shell making process, possibly in combination with frequency shaping filter 1010 and means for maximum power limiting such as a mechanical peak clipper 1004.

Mechanical Peak Clipping

Many applications for HPDs experience strong variations in noise exposure over time. The extreme example is people shooting with guns (military, hunters) where speech communication in-between the actions is strongly desired and where the sound gets very loud for a short time. In active devices such conditions have been solved with so-called "peak clippers" which are fairly easy to implement in electronics and which limit the output of the device independent of the input signal while leaving the signal undistorted for normal noise levels. For a passive device this can be realized by a pressure sensitive valve 1004 opening or blocking the audio canal at the sound inlet.

Acoustical Tubing

Analog to the intelligent passive HPD acoustical shaping, several audio signal enhancements can be pursued by means of acoustical tubing for active HPD devices. Active HPDs are systems where the incoming sound picture is picked up by a transducer microphone system, processed electronically and converted back to acoustical domain by a transducer receiver (loudspeaker). Many properties and artifacts of the signal can be taken care of in the electronic domain, but some remain difficult (e.g. resonance peaks, relation direct (venting) and indirect (processed) sound) and in particular the upcoming challenge of managing wide band receivers (e.g. two-way) for high-fidelity applications. Broadband output transducers 2010 made for such applications produce multiple output signals the mixing of which becomes complex. The ability to determine the shape and length of the individual acoustic tubes 2012 and their mixing point becomes a design and modeling choice at production time. Naturally such a system can be combined with the semi-integrated passive filter mentioned earlier for further degrees of freedom.

Detectable HPD

HPDs are mostly used in industrial environments. In the food processing industry an additional requirement also affects these devices. Any foreign particle (to the food ingredients) must be detectable within the production process. For HPDs this implies that the devices need to contain a certain amount of metal to enable the detection equipment to find it if lost in the production line. Metal can be inserted into HPDs in a number of different ways: for active devices there should be enough metal in the transducers 2002, 2010 and the battery contained in 2002, hence no additional component is needed. In case of passive devices metal can be mixed into the shell base material 1000, a specific metal component 1013 can be mounted in a prepared cavity 1012, the cord adapter faceplate element 1014 can be made of metal and the button part of the on/off switch 1002 can be made of metal. In a HPD with a RFID tag, the tag itself is detectable if the equipment for detection is implemented in the production line.

HPD Wearing Compliance

Wearing of HPDs in industrial environments obliges to regulations in most countries. Assuming that the devices have the desired protective effect when they are worn (most other topics described address this very issue), the wearing itself becomes the compliance control topic. With recent developments in miniaturized RFID (radio frequency identification devices) technology, it becomes feasible to implement such devices into a customized HPD given the shell technology described. The RFID tag 1006, 2006 is inserted into a predefined cavity 1007, 2007 and when the wearer passes through gateways equipped with RFID detection systems, the positions of the two HPDs can be obtained and the control function carried out according to whether a predefined condition regarding the detected positions is fulfilled or not (e.g. separation of the HPDs according to the width of the head and height of the HPDs according to the ear height). As mentioned, the RFIDs can also serve as HPD detection devices in food production processes.

Basic Functions

Functions that conventionally are mounted components, such as a grip handle for insertion and removal of the HPD, can easily be integrated with use of the shell technology. The product design and assembly more and more becomes a software issue and the individual product is increasingly designed to order according to the specific requirements of each customer.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A hearing protection earplug, comprising:
a shell for being worn at least in part in an ear canal of a user and a faceplate at the outer end of said shell or within a cavity of said shell having an outer opening, wherein said faceplate is provided with adapter means for acoustically connecting, in a detachable manner, a measuring hole extending into the interior of said shell with an external measuring tube,
wherein said adapter means are adapted to detachably connect to a removable multi-function plug comprising means for closing said measurement hole and comprise an adapter element fixedly inserted into said measuring hole or provided as a part of said faceplate, the adapter element comprising a thread for engaging with a mating thread provided at said external measuring tube and with a mating thread provided at said multi-function plug, respectively.

2. The hearing protection earplug according to claim 1, wherein said removable multi-function plug comprises means for fastening a security cord.

3. The hearing protection earplug according to claim 1, wherein said removable multi-function plug comprises means for wireless communication with an external communication unit.

4. The hearing protection earplug according to claim 1, wherein said adapter element comprises an outer annular cylindrical flange bearing a male thread, and wherein said adapter plug has a lower rim whose inner cylindrical surface is provided with a female thread for being screwed onto said thread of said adapter element.

5. The hearing protection earplug according to claim 1, wherein said adapter element is at least one of cemented, glued, snapped and bayonet coupled into said measuring hole.

6. The hearing protection earplug according to claim 2, wherein said means for fastening a security cord comprise a tab upstanding from a lower portion of said adapter plug, said tab comprising an eyelet for receiving a security cord.

7. The hearing protection earplug according to claim 1, wherein said measurement hole closing means comprise a cylindrical stem fitting into an axial cylindrical bore of said adapter element.

8. The hearing protection earplug according to claim 1, wherein said shell is provided with a sound attenuation filter device and wherein said faceplate comprises a sound inlet hole.

9. The hearing protection earplug according to claim 8, wherein said filter device is received in said sound inlet hole.

10. The hearing protection earplug according to claim 1, wherein said measuring hole connects to a measurement channel extending into a cavity within said shell or through said shell to the inner end of said shell.

11. The hearing protection earplug according to claim 10, wherein said measurement channel is formed integral with said shell.

12. The hearing protection earplug according to claim 1, wherein said faceplate is formed integral with said shell.

13. The hearing protection earplug according to claim 1, wherein said shell is a customized hard shell having a hardness from shore D 85 to shore D 65 and an outer surface individually shaped according to a measured inner shape of said user's outer ear and ear canal.

14. A multi-function plug to be used with a hearing protection earplug according to claim 1, comprising means for closing said measuring hole and means for fastening a security cord.

15. A multi-function plug to be used with a hearing protection earplug according to claim 1, comprising means for closing said measuring hole and means for wireless communication with an external communication unit.

16. A use of a hearing protection earplug according to claim 1, comprising: removing said multi-function plug from said adapter means, connecting said external measuring tube to said adapter means, performing acoustic measurements via said external measuring tube, removing said external measuring tube from said adapter means and connecting said multi-function plug to said adapter means for closing said measuring hole.

17. A method for manufacturing a hearing protection earplug comprising a shell for being worn at least in part in an ear canal of a user, comprising:
forming said shell,
providing a faceplate at an outer end of said shell or within a cavity of said shell having an outer opening, said faceplate having a measuring hole extending into the interior of said shell,
providing said faceplate with adapter means adapted for acoustically connecting said measuring hole, in a detachable manner, with an external measuring tube and adapted to detachably connect to a removable multi-function plug comprising means for closing said measurement hole, wherein said adapter means comprise an adapter element fixedly inserted into said measuring hole or provided as a part of said faceplate, the adapter element comprising a thread for engaging with a mating thread provided at said external measuring tube and with a mating thread provided at said multi-function plug, respectively.

18. The method according to claim 17, wherein said adapter element is at least one of cemented, glued, snapped and bayonet coupled into said measuring hole.

19. The method according to claim 17, wherein said faceplate is formed integral with said shell.

20. The method according to of claim 17, wherein said adapter means is formed integral with said shell.

21. The method according to claim 17, wherein an inner shape of said user's outer ear and ear canal is measured and an outer shape of said shell is individually determined according to said measured inner shape of said user's outer ear and ear canal.

* * * * *